(12) United States Patent
Hamano et al.

(10) Patent No.: US 7,147,844 B2
(45) Date of Patent: Dec. 12, 2006

(54) SYSTEM FOR STABILIZING LACRIMAL FLUID LAYER

(75) Inventors: Takashi Hamano, Ashiya (JP); Kenji Morishima, Osaka (JP); Norihisa Hatano, Osaka (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 332 days.

(21) Appl. No.: 10/168,812

(22) PCT Filed: Dec. 26, 2000

(86) PCT No.: PCT/JP00/09239

§ 371 (c)(1),
(2), (4) Date: Jun. 24, 2002

(87) PCT Pub. No.: WO01/47532

PCT Pub. Date: Jul. 5, 2001

(65) Prior Publication Data

US 2003/0021829 A1    Jan. 30, 2003

(30) Foreign Application Priority Data

Dec. 27, 1999  (JP) ................................. 11-369747

(51) Int. Cl.
*A61K 31/74*  (2006.01)

(52) U.S. Cl. .................................................. 424/78.04
(58) Field of Classification Search .............. 424/78.04
See application file for complete search history.

(56) References Cited

U.S. PATENT DOCUMENTS

| 3,959,102 A | 5/1976 | Wajs et al. |
| 5,591,426 A | 1/1997 | Dabrowski et al. |
| 6,180,093 B1 * | 1/2001 | De et al. ................ 424/78.04 |

FOREIGN PATENT DOCUMENTS

| WO | WO 98/11875 A | 3/1998 |
| WO | WO 98/32421 A1 | 7/1998 |

\* cited by examiner

*Primary Examiner*—Carlos A. Azpuru
(74) *Attorney, Agent, or Firm*—Frishauf, Holtz, Goodman & Chick, P.C.

(57) ABSTRACT

A purpose of the present invention is to remove dryness and unpleasantness in eyes of contact lens wearers and to obtain favorable moist feel and wearing feel by stabilizing a lacrimal fluid layer on the surface of eyeballs of the wearers. By using an ophthalmic composition containing polyvinyl pyrrolidone, the lacrimal fluid layer existing on ionic contact lenses can be stabilized via adsorption of polyvinyl pyrrolidone on the ionic contact lenses. By adding a viscosity-increasing agent to the ophthalmic composition, the lacrimal fluid layer can be maintained in a stable state over a long period of time.

13 Claims, No Drawings

SYSTEM FOR STABILIZING LACRIMAL FLUID LAYER

This application is a U.S. National Phase Application under 35 U.S.C. 371 of International Application No. PCT/JP00/09239 filed Dec. 26, 2000.

TECHNICAL FIELD

The present invention relates to a system for stabilizing a lacrimal fluid layer to remove dryness and unpleasantness in eyes of contact lens wearers and to obtain good moist feel and wearing feel by stabilizing the lacrimal fluid layer existing on the contact lenses (i.e. on the front and rear faces of the lenses) in wearing the contact lenses.

BACKGROUND ART

Contact lenses have been popularized remarkably in recent years, and not only hard contact lenses and soft contact lenses but also disposable contact lenses are widely used. These contact lenses are classified into ionic and nonionic contact lenses, and materials of the ionic contact lenses to be used are polymers (or copolymers) obtained by polymerizing (or copolymerizing) hydroxyethyl methacrylate, methyl methacrylate, methacrylic acid and the like.

Since a lacrimal fluid layer existing on a front face of contact lenses in wearing and a lacrimal fluid layer existing between a rear face of the contact lenses and the surface of eyeballs are very thin and unstable, a lacrimal fluid on the surface of the eyeballs of the wearers disappears faster than those of persons who do not wear contact lenses. As a result, the lacrimal fluid on the surface of the eyeballs often becomes deficient at short intervals when the wearers blink, and feel in wearing the contact lenses deteriorates, i.e. dryness and unpleasantness in eyes occur. Further, chronic deficiency of the lacrimal fluid on the surface of the eyeballs of the wearers is responsible for serious disorders in external eye segment such as conjunctiva and cornea.

The very thin lacrimal fluid layers existing on the front and rear faces of the contact lenses in wearing work as cushions on the eyeballs and eyelids of the wearers. Accordingly, a system to maintain the lacrimal fluid layer on the surface of the eyeballs of the wearers in a stable state is required in order to improve the wearing feel and prevent the disorders from occurring in the external eye segment such as conjunctiva and cornea.

DISCLOSURE OF THE INVENTION

Focusing attention on ionic contact lenses spreading widely, and studying precisely a relation between adsorptivity of various high molecular compounds on the ionic contact lenses and a moist feel and wearing feel in eyes of wearers of the ionic contact lenses, the present inventors found that polyvinyl pyrrolidone is adsorbed on the ionic contact lenses specifically, it has an effect on removing dryness and unpleasantness in the eyes of the wearers, and it is excellent in instilling feel when it is used as an ophthalmic solution. Further, the present inventors found that water retention of the ionic contact lenses is improved by using an ophthalmic composition formulated with polyvinyl pyrrolidone and a viscosity-increasing agent, and as a result, it is possible to sustain the above-mentioned improving effects in the eyes of the wearers over a long period of time.

Namely, the present invention relates to a system comprising the ophthalmic composition containing polyvinyl pyrrolidone, preferably an ophthalmic composition containing polyvinyl pyrrolidone having an average molecular weight of 500,000 or lower in an amount of 0.05 to 3.0% by weight, and stabilizing a lacrimal fluid layer existing on the ionic contact lenses (on the front and rear faces of the lenses) by adsorbing polyvinyl pyrrolidone on the ionic contact lenses. Use of the ophthalmic composition containing polyvinyl pyrrolidone can not only improve the moist feel and wearing feel in the eyes of the wearers but also prevent disorders from occurring in external eye segment such as conjunctiva and cornea.

By using the ophthalmic composition containing polyvinyl pyrrolidone and the viscosity-increasing agent, the adsorption of polyvinyl pyrrolidone on the faces of the contact lenses is sustained over a long period of time, and the water retention of the contact lenses is improved. Accordingly, for example, when the above-mentioned ophthalmic composition is used as an ophthalmic solution, instillation times can also be reduced.

The present invention relates to a system for stabilizing the lacrimal fluid layer existing on the contact lenses by neutralizing a negative charge of the contact lenses with a positive charge of polyvinyl pyrrolidone adsorbed on the front and rear faces of the contact lenses by making the ophthalmic composition containing polyvinyl pyrrolidone having the positive charge act on the contact lenses having the negative charge. It is inferred that such a stabilized lacrimal fluid layer removes the dryness and unpleasantness in the eyes of the wearers, and the ophthalmic composition exhibits good feel in instilling when the composition is used as an ophthalmic solution.

By adding the viscosity-increasing agent besides polyvinyl pyrrolidone, which is an essential ingredient, to the ophthalmic composition of the present invention, the lacrimal fluid layer existing on the contact lenses can be maintained in a stable state over a long period of time, and good moist feel and wearing feel can be sustained.

Polyvinyl pyrrolidone of the present invention is not particularly limited and desirably has an average molecular weight of 500,000 or lower. This is because an amount of polyvinyl pyrrolidone to be adsorbed on the contact lenses decreases when the average molecular weight of polyvinyl pyrrolidone exceeds 500,000. An amount of polyvinyl pyrrolidone is desirably 0.05 to 3.0% by weight. This is because the ophthalmic composition sometimes becomes too viscous when the amount of polyvinyl pyrrolidone exceeds 3.0% by weight, and a lacrimal fluid cannot be adsorbed on the lenses sufficiently and satisfactory moist feel and wearing feel cannot be obtained when the amount is less than 0.05% by weight. The amount of polyvinyl pyrrolidone is more preferably 0.5 to 2.0% by weight, the most preferably 0.8 to 1.2% by weight.

Examples of the viscosity-increasing agent of the present invention are methyl cellulose, hydroxypropyl methylcellulose, polyvinyl alcohol, sorbitol, sodium carboxymethyl cellulose, hydroxyethyl cellulose, triisopropanolamine and the like. The viscosity-increasing agent is not particularly limited so far as it is an additive having a thickening action. When hydroxypropyl methylcellulose (HPMC) is used as the viscosity-increasing agent, it is desirable to add it in the range of 0.01 to 1.0% by weight. This is because the ophthalmic composition is too viscous when the amount of hydroxypropyl methylcellulose exceeds 1.0% by weight. The amount of hydroxypropyl methylcellulose is more preferably 0.05 to 0.5% by weight, the most preferably 0.1 to 0.3% by weight.

It is possible to add a pharmaceutically acceptable additive such as the above-mentioned viscosity-increasing agent; an isotonic agent such as sodium chloride, potassium chloride, calcium chloride, glycerin or propylene glycol; a buffer such as boric acid, Sodium borate, citric acid, disodium hydrogenphosphate or ε-aminocaproic acid; a preservative such as benzalkonium chloride, chlorohexidine gluconate, benzethonium chloride, sorbic acid, potassium sorbate, ethyl paraoxybenzoate or butyl paraoxybenzoate; or a stabilizing agent such as disodium edetate, besides polyvinyl pyrrolidone to the ophthalmic composition of the present invention.

The most preferred examples of the ophthalmic composition of the present invention are an ophthalmic solution and a wearing solution containing polyvinyl pyrrolidone in an amount of 0.8 to 1.2% by weight and hydroxypropyl methylcellulose in an amount of 0.1 to 0.3% by weight. When the present composition is used as the ophthalmic solution or the wearing solution, it is preferable to add, for example, disodium edetate in an amount of 0.05 to 0.3% by weight as the stabilizing agent and sorbic acid or a salt thereof in an amount of 0.05 to 0.3% by weight as the preservative.

When the present ophthalmic composition is used as an ophthalmic solution for contact lenses, it is preferable to adjust pH at about 7.0 with the general buffer such as boric acid or Sodium borate and adjust an osmotic pressure ratio at about 1.0 with the general isotonic agent such as potassium chloride or calcium chloride.

When the present ophthalmic composition is used as an ophthalmic solution for contact lenses, its kinematic viscosity is preferably 1 to 8 $mm^2/s$. When the composition is used as a wearing solution for contact lenses, its kinematic viscosity is preferably 1 to 50 $mm^2/s$.

When the present ophthalmic composition is used as an ophthalmic solution, the ophthalmic solution can usually be instilled twice to five times per day (one to three drops at a time). One or two drops of the present composition can be added dropwise to the contact lenses in wearing. When the present ophthalmic composition is used as a wearing solution, the contact lenses are immersed in the wearing solution before wearing. Further, the present ophthalmic composition can be used also as a preserving solution or a cleaning solution for contact lenses.

BEST MODE FOR CARRYING OUT THE INVENTION

The present invention is described by giving Examples below, but the present invention is not limited to these Examples.

EXAMPLES

1. Test of Adsorption on Ionic Contact Lens

An ionic contact lens (ionic and high water content lens: One Day Acuvue, material: hydroxyethyl methacrylate-methacrylic acid copolymer) was immersed in each solution prepared by dissolving polyvinyl pyrrolidone (PVP) having K values of 15, 30 and 90 respectively, methyl cellulose (MC) and polyvinyl alcohol (PVA) in phosphate buffer having pH of 7.0, the lens was preserved in the solution at 40° C. for three hours, and then each concentration of the high molecular compound in the solution was measured to calculate each adsorption amount of the high molecular compound. Table 1 shows each amount of the high molecular compound adsorbed on the contact lens (CL).

TABLE 1

|  | Test 1 | Test 2 | Test 3 | Reference 1 | Reference 2 |
|---|---|---|---|---|---|
| High molecular compound | PVP K value: 15 | PVP K value: 30 | PVP K value: 90 | MC | PVA |
| Adsorption amount (μg/CL) | 258.9 | 329.4 | 61.3 | 7.2 | 8.4 |

2. Components of Ophthalmic Solutions and Test of Instilling Feel

Ophthalmic solutions having formulation components shown in Examples 1 to 5 and Comparative Example 1 were prepared according to Table 2 by the conventional process. Disodium edetate (0.1 g) was added as a stabilizing agent, sorbic acid (0.1 g) was added as a preservative, and pH and an osmotic pressure ratio were adjusted to 7.0 and 1.0 respectively. Next, each ophthalmic solution having the formulation in Examples 1 to 5 and Comparative Example 1 was instilled once (two or three drops) into each subject wearing ionic contact lenses, and scoring was conducted with regard to an effect on improving a moist feel, an effect on sustaining the moist feel and an effect on improving feel in wearing the contact lenses (CL) according to the evaluating criterion shown below. The obtained scores are the average of six samples. Table 2 shows components of each ophthalmic solution and results of the test of feel in instilling each ophthalmic solution.

Evaluating Criterion

5: improving effect and sustaining effect were remarkable.

4: improving effect and sustaining effect were recognized.

3: improving effect and sustaining effect were somewhat recognized.

2: no change.

1: improving effect and sustaining effect rather deteriorated.

TABLE 2

| Main components (g/100 ml) | Examples | | | | | Comparative Example |
|---|---|---|---|---|---|---|
|  | 1 | 2 | 3 | 4 | 5 | 1 |
| PVP [K value: 30] | 1.0 | 1.0 | 1.0 | 1.0 | 0.8 | — |
| HPMC 2910 [50] | 0.3 | — | 0.1 | — | 0.3 | — |
| HPMC 2910 [4,000] | — | 0.3 | — | — | — | — |
| Kinematic viscosity at 30° C. ($mm^2/s$) | 2.0 | 6.4 | 1.3 | 1.0 | 2.0 | 0.9 |
| Effect on improving moist feel | 4.0 | 4.0 | 4.3 | 4.0 | 3.8 | 2.2 |
| Effect on sustaining moist feel | 4.2 | 4.0 | 4.3 | 3.7 | 3.5 | 2.0 |
| Effect on improving pleasantness in wearing CL | 4.2 | 3.8 | 4.0 | 3.7 | 3.7 | 1.8 |

HPMC in the table means hydroxypropylmethyl cellulose.

3. Test of Water Retention of Ionic Contact Lens

Tests of water retention of an ionic contact lens were carried out with the lapse of time for the ophthalmic solution of Example 3 and physiological saline. Namely, moisture on the surface of the ionic contact lens (trade name: One Day Acuvue) was wiped off, and the lens was placed on a laboratory dish. Closing the dish with a cover, the lens was weighed and then dried in a drying oven at 40° C. for 30 minutes. It was confirmed that a water content of the lens calculated by weighing the dried lens was almost the same as that shown by the lens maker. Next, the ophthalmic solution of Example 3 and physiological saline were taken in three ml portions, each solution was introduced into a 6 ml glass bottle, and the above-mentioned dried ionic contact lens was immersed in each solution at 35° C. for one day. Moisture on the surface of the lens was wiped off, and the lens was placed on a laboratory dish. Closing the dish with a cover, the lens was weighed. The laboratory dish was preserved in a thermo-hygrostat at a temperature of 25° C. and relative humidity of 60% after opening it, and the lens was taken out at a regular time intervals (six times every 10 minutes) and weighed. Table 3 shows results obtained by calculating a water retention rate (water remaining rate) of the ionic contact lens according to the following equation. Numerical values in the table are the average of three samples.

Water remaining rate (%)=100−[($Wi$−$Wc$)−($Ws$−$Wc$)/($Wi$−$Wc$)×100]

Wi: weight of contact lens after finishing immersion
Ws: weight of contact lens after taking out lens
Wc: weight of contact lens after drying lens

TABLE 3

| Storage period | Ophthalmic solution of Example 3 | Physiological saline |
|---|---|---|
| 10 minutes | 88% | 39% |
| 20 minutes | 56% | 21% |
| 30 minutes | 41% | 15% |
| 40 minutes | 34% | 12% |
| 50 minutes | 26% | 5% |
| 60 minutes | 16% | 1% |

Table 1 clearly shows that polyvinyl pyrrolidone (PVP) is specifically adsorbed on the ionic contact lens. In particular, PVPs having K values of 15 and 30 are well adsorbed. Table 2, showing the results of the test of feel in instilling each ophthalmic solution, shows that the present ophthalmic composition containing PVP stabilizes a lacrimal fluid layer existing on the ionic contact lens and improves the instilling feel (i.e. moist feel and wearing feel). Further, combining hydroxypropyl methylcellulose (HPMC) with the ophthalmic composition containing PVP, the instilling feel is much improved and sustained. Accordingly, instillation times can be reduced. Table 3, showing the results of the water retention test, shows that the ophthalmic composition of the present invention improves the water retention of the ionic contact lens remarkably compared with physiological saline. Accordingly, since PVP is adsorbed on the contact lenses and has an effect on stabilizing the lacrimal fluid layer on the surface of the contact lenses and maintaining a lacrimal fluid over a long period of time, the ophthalmic composition of the present invention can improve the moist feel and wearing feel of the ionic contact lens wearers as well as prevent disorders from occurring in external eye segment such as conjunctiva and cornea.

Industrial Applicability

The present invention relates to a system for stabilizing a lacrimal fluid layer to remove dryness and unpleasantness in eyes of contact lens wearers and to obtain good moist feel and wearing feel by stabilizing the lacrimal fluid layer existing on the contact lenses (i.e. on the front and rear faces of the lenses) in wearing the contact lenses.

The invention claimed is:

1. A method for maintaining a lacrimal fluid layer existing on an ionic contact lens in a stable state in an eye over a long period of time wherein polyvinyl pyrrolidone is adsorbed on an ionic contact lens sustainingly, comprising applying an ophthalmic composition to be in contact with an ionic contact lens in an eye, the ophthalmic composition consisting of polyvinyl pyrrolidone and a viscosity-increasing agent.

2. The method as claimed in claim 1, wherein the viscosity-increasing agent is hydroxypropyl methylcellulose.

3. A method for maintaining a lacrimal fluid layer existing on an ionic contact lens in a stable state in an eye over a long period of time wherein polyvinyl pyrrolidone is adsorbed on an ionic contact lens sustainingly, comprising applying an ophthalmic composition to be in contact with an ionic contact lens in an eye, the ophthalmic composition consisting of polyvinyl pyrrolidone having an average molecular weight of 500,000 or lower in an amount of 0.05 to 3.0% by weight and hydroxypropyl methylcellulose in an amount of 0.01 to 1.0% by weight.

4. A method for maintaining a lacrimal fluid layer existing on an ionic contact lens in a stable state in an eye over a long period of time wherein polyvinyl pyrrolidone is adsorbed on an ionic contact lens sustainingly, comprising applying an ophthalmic composition to be in contact with an ionic contact lens in an eye, the ophthalmic composition consisting of polyvinyl pyrrolidone having an average molecular weight of 500,000 or lower in an amount of 0.5 to 2.0% by weight and hydroxypropyl methylcellulose in an amount of 0.05 to 0.5% by weight.

5. The method as claimed in claims 1 to 3, wherein the ionic contact lens is made of a material which is a polymer or a copolymer obtained by homopolymerizing or copolymerizing hydroxyethyl methacrylate.

6. The method as claimed in claims 1 to 4, wherein the ophthalmic composition has a kinematic viscosity of 1 to 50 $mm^2/s$.

7. An ophthalmic solution and a solution for wearers of contact lenses consisting of polyvinyl pyrrolidone and a viscosity increasing agent, and which is for applying to an eye of a subject wearing an ionic contact lens.

8. An ophthalmic solution and a solution for wearers of contact lenses consisting of polyvinyl pyrrolidone in an amount of 0.5 to 2.0% by weight, hydroxypropyl methylcellulose in an amount of 0.05 to 0.5% by weight, sorbic acid or a salt thereof in an amount of 0.05 to 0.3% by weight and disodium edetate in an amount of 0.05 to 0.3% by weight.

9. The ophthalmic solution as claimed in claim 7, wherein the viscosity-increasing agent is hydroxypropyl methylcellulose.

10. The ophthalmic solution as claimed in claim 9, wherein the polyvinyl pyrrolidone has an average molecular weight of 500,000 or lower and is in an amount of 0.05 to 3.0% by weight; and the hydroxypropyl methylcellulose is in an amount of 0.01 to 1.0% by weight.

11. The ophthalmic solution as claimed in claim 10, wherein the polyvinyl pyrrolidone is in an amount of 0.5 to 2.0% by weight and the hydroxypropyl methylcellulose is in an amount of 0.05 to 0.5% by weight.

12. The ophthalmic solution as claimed in claim 11, wherein the ophthalmic solution has a kinematic viscosity of 1 to 50 $mm^2/s$.

13. The method as claimed in claim 10, wherein the polyvinyl pyrrolidone is in an amount of 0.8 to 1.2% by weight; and the hydroxypropyl methylcellulose is in an amount of 0.1 to 0.3% by weight.

* * * * *